US006316694B1

(12) United States Patent
Dormann et al.

(10) Patent No.: US 6,316,694 B1
(45) Date of Patent: Nov. 13, 2001

(54) TRANSFORMED EMBRYOGENIC MICROSPORES FOR THE GENERATION OF FERTILE HOMOZYGOUS PLANTS

(75) Inventors: Mathias Dormann; Hung-Mei Wang; Michael Oelck, all of Saskatoon (CA)

(73) Assignee: AgrEvo Canada, Inc., Saskatchewan (CA)

( * ) Notice: Subject to any disclaimer, the term of this patent is extended or adjusted under 35 U.S.C. 154(b) by 0 days.

(21) Appl. No.: 08/913,398

(22) PCT Filed: Mar. 15, 1996

(86) PCT No.: PCT/EP96/01140

§ 371 Date: Nov. 14, 1997

§ 102(e) Date: Nov. 14, 1997

(87) PCT Pub. No.: WO96/29419

PCT Pub. Date: Sep. 26, 1996

(30) Foreign Application Priority Data

Mar. 17, 1995 (EP) .................................................. 95103961

(51) Int. Cl.$^7$ .......................... C12N 15/82; C12N 15/84; C12N 5/04; A01H 4/00
(52) U.S. Cl. ......................... 800/278; 800/290; 800/294; 800/295; 800/298; 800/306; 435/469; 435/471; 435/410
(58) Field of Search ................................ 435/172.3, 410, 435/69.1, 70.1, 71.1, 468, 469, 471, 418, 419, 420; 800/205, 278, 290, 294, 295, 298, 306

(56) References Cited

U.S. PATENT DOCUMENTS 5,445,961   8/1995   Genovesi et al. .................... 800/276

FOREIGN PATENT DOCUMENTS

| 1327173 | 2/1994 | (CA) . |
| 0 203790 | 12/1986 | (EP) . |
| 0 301 316 | 2/1989 | (EP) . |
| 0 483 847 | 5/1992 | (EP) . |
| 8801444 | 1/1990 | (NL) . |
| WO 92/09696 | 6/1992 | (WO) . |
| WO 92/12250 | 7/1992 | (WO) . |
| WO 92/14828 | 9/1992 | (WO) . |

OTHER PUBLICATIONS

Barrett et al. Plant Cell Tissue Organ Culture. 1997. vol. 47: 135–144.*
Pechan. Plant Cell reports. 1989. vol. 8: 387–390.*
Laursen et al. Plant Molecular Biology. 1994. vol. 24: 51–61.*
Davis et al. Methods in Molecular Biology. Elsevier. 1986. Chapter 8–2, p. 93.*
Jardinaud et al. Plant Science. 1993. vol. 93: 177–198.*
Potrykus. Ann. Review of Plant Physiol. 1991. vol. 42: 205–225.*
Napoli et al. The Plant Cell. 1989. vol. 2: 278–289.*
Carvalho et al. The EMBO Journal. 1992. vol. 11: 5995–5602.*
Poulsen (1996) "Genetic Transformation of Brassica" Plant Breeding 115:209–225.
Takasaki et al. (1997) "Factors Influencing Agrobacterium—Mediated Transformation of *Brassica rapa* L" Breeding Science 47:127–134.
Potrykus (1993) "Gene Transfer to Plants: approaches and available techniques" Plant Breeding: Principles and prospects. Eds. Hayward et al., Chapman & Hall London pp. 126–137.
Walden et al. (1995) "Gene–transfer and plant regeneration techniques" Tibtech 13:324–331.
Agricell Report (1994). Nov. issue. p. 34.
Theor Appl Genet (1987) vol. 75, pp. 30–36.
Plant Cell Reports (1992) vol. 11, pp. 567–570.
Plant Cell Reports (1990) vol. 8. pp. 680–683.
Theor Appl Genet (1989) vol. 78: 831–835.
Plant Science (1993) vol. 93, pp. 177–184.
Biol. Abstract No. 20995.
Biol. Abstract No. 60259.
Database "Indian J Biochem Biophys".
Plant Cell, Tissue and Organ Culture (1995) vol. 40, pp. 97–100.
Plant Cell Reports (1992) vol. 11, pp. 234–237.
Plant Cell Reports (1989) vol. 8, pp. 387–390.
Theor Appl Genet (1989) vol. 78, pp. 831–835.
Plant Cell Tissue and Organ Culture (1991) vol. 25, pp. 209–218.
In Vitro Cell. Dev. Biol. (1992) vol. 28, pp. 53–58.

* cited by examiner

Primary Examiner—Paula K. Hutzell
Assistant Examiner—O. M. F. Zaghmout
(74) Attorney, Agent, or Firm—Frommer Lawrence & Haug LLP

(57) ABSTRACT

The invention relates to transformed, embryogenic microspores and progeny thereof characterized by being transformed by *Agrobacterium tumefaciens*, capable of leading to non-chimeric transformed haploid or doubled haploid embryos that develop into fertile homozygous plants within one generation and containing stably integrated into their genome a foreign DNA, said DNA being characterized in that it comprises at least one gene of interest and at least base pairs within the right border sequence of Agrobacterium T-DNA. The invention furthermore relates to a method for the incorporation of foreign DNA into chromosomes of microspores comprising the following steps: a) infecting of embryogenic microspores with Agrobacteria, which contain plasmid carrying a gene of interest under regulatory control of initiation and termination regions bordered by at least one T-DNA border, b) Washing out and killing the Agrobacteria after co-cultivation.

8 Claims, 2 Drawing Sheets

Figure 1:
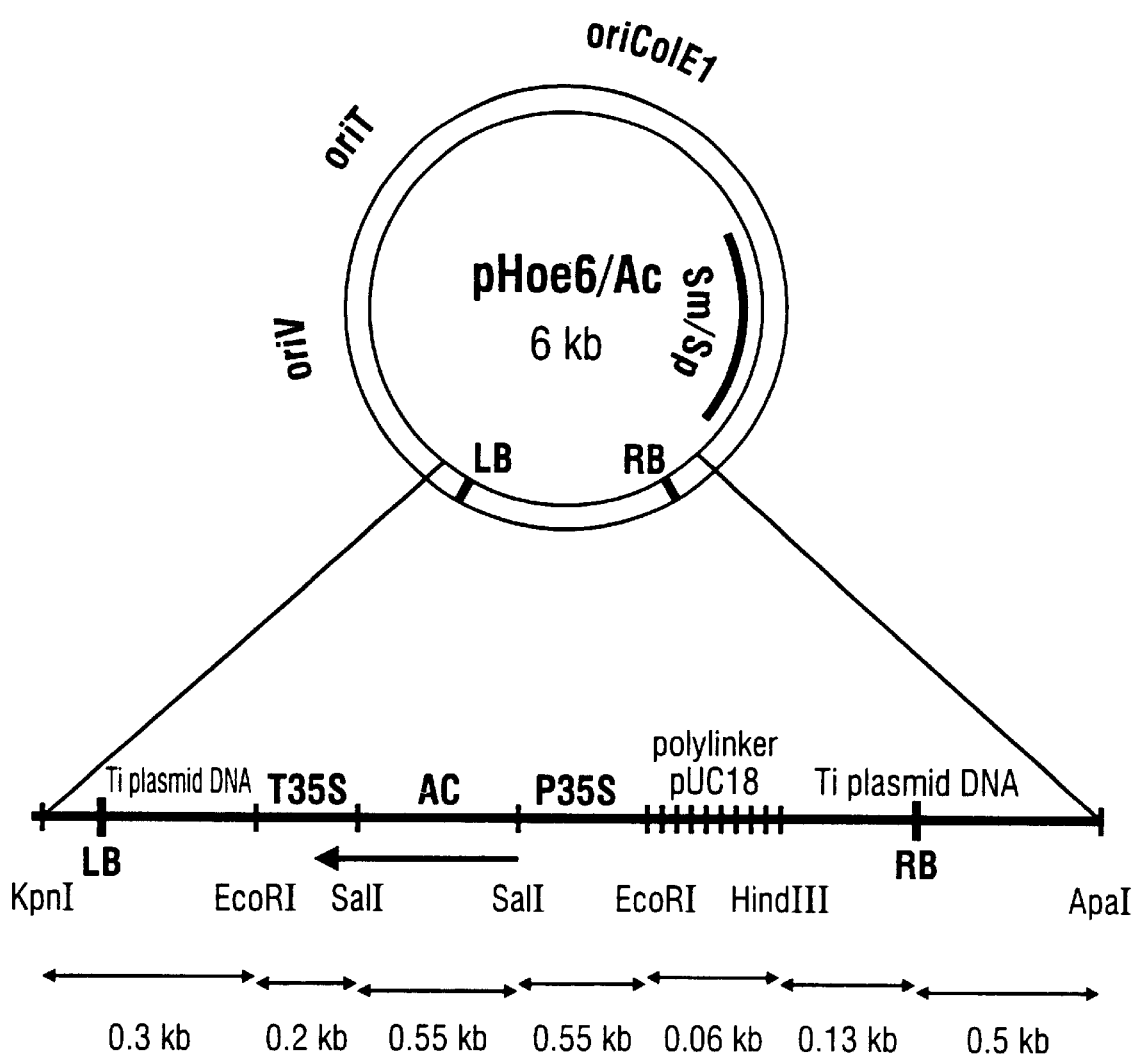

TRANSFORMED EMBRYOGENIC MICROSPORES FOR THE GENERATION OF FERTILE HOMOZYGOUS PLANTS

1. INTRODUCTION

Transgenic crop plants can be produced using different transformation techniques. The method of choice for species and varieties, where plant regeneration from tissue culture is efficient, is Agrobacterium (Potrykus 1993). The *Agrobacterium tumefaciens* transformation system is simple and inexpensive (DeBlock 1993). It is the most effective method of transferring foreign DNA into a host plant (Thierfelder et al. 1993). Plants are obtained with a limited number of gene insertions, and usually insertion of DNA occurs between two defined border sequences completely and exclusively (DeBlock 1993). It is therefore not surprising that in terms of use and apparent progression to field trials, the majority of gene transfer experiments have involved the Agrobacterium system (White 1993).

Microspores of higher plants have the potential to develop, under appropriate conditions directly into haploid or doubled haploid plants. Microspores of higher plants develop in vivo into pollen grains (gametophytic pathway). Microspore culture can induce an alternative (sporophytic) pathway which leads to the formation of haploid and doubled haploid embryos. These embryos develop directly into normal fertile plants. Misunderstandingly these embryos are sometimes referred to as pollen embryos.

The time saving for the breeder working with microspore transformants compared to transformants from heterozygous plant material is estimated to be three years for the development of each transgenic variety. This is due to the immediate fixation of the genes in the homozygous doubled haploid lines. This allows a more efficient selection of agronomic and quality traits and the immediate testing of combining ability for the development of hybrid cultivars.

Therefore, since embryogenic microspores develop into homozygous fertile plants and are single haploid cells, they are theoretically the most suitable recipients for gene transfer (Huang and Keller 1989).

Several laboratories (Potrykus 1991, Heberle-Bors 1995) have unsuccessfully attempted transforming microspores with Agrobacterium and Sangwan et al. (1993) have concluded that "it is difficult if not impossible to obtain transgenic plants by infection of pollen or proembryos with Agrobacterium." Interestingly Heberle-Bors (1995) summarizes his attempts to transform microspores stating that A. tumefaciens was not suitable to transfer DNA into microspores, contrary to his 1989 patent. The thick cell wall of microspores has been perceived to be inaccessible to Agrobacterium (Stöger et al. 1995, Jones-Villeneuve et al. 1995).

More frequently, multicellular haploid tissues such as microspore-derived embryos; (Neuhaus et al. 1987, Swanson and Erickson 1989, Huang 1992) or haploid stem segments (Arnoldo 1992) have been used.

A common misconception is the difference between microspores and microspore-derived embryos where doubled-haploid plants can be obtained from both. Microspores are single cells and can be stimulated to produce embryos. The transformation of microspores leads to non-chimeric embryos and then plants. On the other hand microspore-derived embryos are multi-celled tissues. The transformation of microspore-derived embryo segments may lead to chimeric sectors from which chimeric shoots or secondary embryos can be selected. In addition somaclonal variation is not uncommon as there is usually an intermediate callus phase associated with regeneration from microspore-derived embryo segments.

The closest report of the prior art is the publication of Pechan (1989) on microspore co-cultivation with Agrobacterium. He claimed the production of kanamycin and hygromycin resistant plants but did not prove DNA integration or the sexually transmissibility of the transgene and furthermore, the described method has not been reproducible by others (Huang 1992).

Several reports describe the use of transformation techniques on microspores. Huang (1992) reported the use of microinjection, particle bombardment and electroporation on microspores and observed some transient gene expression, but no stable transformants. The review also described the use of Agrobacterium on microspores and in over 50 experiments conducted, only one plant was regenerated where Agrobacteria were present at the proembryo stage and the event could not be reproduced. Jardinaud et al. (1993) reported only transient gene expression in experiments using electroporation on B. napus microspores and using biolistics on maize microspores (Jardinaud 1995). Microinjection has also been attempted in B. napus microspores but this was not successful (Jones-Villeneuve et al. 1995).

Particle bombardment is the only method used on embryogenic microspores that has led to the production of stable transformed plants (Jähne et al. 1994, Stöger et al. 1995). However in comparing different transformation methods, Christou (1995) concluded that with biolistics, the underlying mechanism of the gene transfer process is not known and the impossibility to control DNA content and integration patterns is a major drawback. Transformed plants normally have multi-copy (Jähne et al. 1994) and random fragmented DNA insertions, that may or may not contain the complete gene of interest.

For breeding purposes, single copy gene insertions are desirable as they can be selected easily and followed through generations with ease and gene expression is good. In addition the plant does not need to transcribe more than the necessary enzymes and phenomena such as co-suppression, i.e. the down regulation of a gene by additional copies of this gene having substantial homology (WO 90/12084), as wastes of valuable plant energy is not a consideration.

The optimal transformation vector to allow single copy gene insertions with defined border sequences is to make use of the naturally occuring transformation process of *Agrobacterium tumefaciens*.

We surprisingly found that microspore transformation via A. tumefaciens is practicable and leads to fertile homozygous plants with predominantly single copy inserts which have been confirmed via Southern blots in B. rapa and B. napus genotypes. Thus fertile homozygous plants with single copy inserts can be produced in only one gene ration using embryogenic microspores and A. tumefaciens.

2. DESCRIPTION OF THE INVENTION

The present invention is directed to transformed embryogenic microspores. The invention additionally provides an improved process for the Agrobacterium mediated transformation.

The invention is directed to transformed, embryogenic microspores and progeny thereof characterized by a) being transformed by *Agrobacterium tumefaciens*, b) capable of leading to non-chimeric transformed haploid or doubled haploid embryos that develop into fertile homozygous plants within one generation and c) containing stably integrated into their genome a foreign DNA, said DNA being characterized in that it comprises at least one gene of interest and at least base pairs within the right border sequence of Agrobacterium T-DNA.

The invention is furthermore directed to microspores containing integrated foreign DNA wherein the gene of interest is bordered by at least base pairs within the right border and parts or all of the left border sequence leading to the specified insertion of the gene(s) of interest. Especially preferred are microspores containing at least one insert of said foreign DNA.

The invention also encompasses transformed, embryogenic microspores capable of being produced according to a process comprising the following steps:

a) infection of embryogenic microspores with Agrobacteria b) washing out and killing the Agrobacteria after co-cultivation during transformation.

Preferably, the Agrobacteria are removed by washing with mucolytic enzymes after co-cultivation and the process comprises the further step of adding cellolytic enzymes during transformation.

The invention is also directed to a method for the incorporation of foreign DNA into chromosomes of microspores comprising the following steps:

a) infecting of embryogenic microspores with Agrobacteria, which contain plasmids carrying a gene of interest under regulatory control of initiation and termination regions bordered by at least one T-DNA border, b) washing out and killing the Agrobacteria after co-cultivation.

Especially preferred is a method wherein the Agrobacteria are removed by washing with mucolytic enzymes after co-cultivation, and in which the gene of interest is bordered by at least one T-DNA border as well as a method leading to the specific insertion of the gene of interest.

The invention further comprises transgenic microspore derived plants comprising a foreign genetic construct inserted into the microspores by the method described above.

According to the invention the transformed embryogenic microspores develop into transgenic homozygous fertile plants within one generation. In a preferred embodiment of the invention the microspores carry only few copy inserts, especially preferred one to three inserts, most favourably only a single copy insert.

One of the major advantages of the process according to instant invention is the transfer of a defined sequence starting within the right border sequence of the T-DNA.

More particularly the present invention covers transformed embryogenic microspores which develop into plants and are characterized by:

a. Being transformed by *A. tumefaciens* b. Expressing mainly single copy inserts c. Leading to non-chimeric transformed haploid or doubled haploid (homozygous) embryos that develop into fertile plants within one generation.

The transformed, embryogenic microspores are obtainable by a process comprising the following steps:

a infection of embryogenic microspores with Agrobacteria b addition of cellolytic enzymes during Agrobacterium co-cultivation c wash with mucolytic enzymes after co-cultivation to kill the Agrobacteria to increase the number of surviving transformants.

The term cellolytic enzyme used hereafter refers to any substance which dissolves cell wall components of the explant inducing a wound response or detergent effect which faciliates gene transfer, i.e. cellulase, hemicellulase, pectinase.

The term mucolytic enzyme used hereafter refers to any substance which dissolves prokaryotic cell wall components (mureines, peptidoglycanes), i.e. lysozyme.

The cellolytic enzymes applied during cocultivation are selected on basis of their capacity of a.) to increase the efficiency of transformation (detergent effect) and b.) to increase the yield of recoverable transformed plantlets. Besides improving transformation efficiency they help to overcome the detrimental effect of longer co-cultivation with Agrobacteria (aggregation and overgrowth of explants) by dissolving selectively the fibrils produced by Agrobacterium during the coculture.

In a preferred embodiment the invention covers transgenic embryogenic microspores produced by the process involving cellulase and lysozyme to enhance the transformation efficiency.

The solutions containing the lytic enzymes contain preferably from about 0.0004 to about 0.1%, most preferably from about 0.004 to about 0.01% of the cellulose and preferably from about 0.1 to about 10%, especially prefered from about 0.5 to about 5% and most preferably from about 0.75 to 1.5% lysozyme.

The concentrations to be used depend on the length of incubation. The used cellulase concentration apply to an incubation period of 3 days. Accordingly, higher concentrations may be used if the incubation period is shorter.

The active enzymes used according the present invention are normally applied in form of compositions together with one or more acceptable supplements, and car be applied to the embryogenic microspores to be treated, simultaneously or in succession, with further compounds.

These compounds can be antimicrotubule active compounds like colchicine (Möller et al. 1994) or trifluralin (Zhao and Simmonds 1995) that lead directly to an in vitro duplication of the haploid microspore genome, which may additionally affect transformation efficiency by synchronizing the cell cycle of the microspores.

They can also be buffer substances or mixtures of several of these preparations, if desired together with further medium supplements customaily employed in the art of transformation.

Suitable media can be semisolid or liquid and correspond to the substances ordinarily employed in transformation technology, e. g. B5 medium (GAMBORG et al. 1968).

The number of applications and the rate of application depend on the Agrobacterium strain and its culture, the time and temperature during cocultivation and the microspore material, i.e. the species or cultivars.

Another object of this invention is to provide a new process for transforming embryogenic microspores which comprises at least one additional washing step with mucolytic enzymes after co-cultivation with Agrobacterium. The washing procedure may be performed preferably as described in materials and methods. Said washing is repeated preferably one to two times.

The solution which may be used to wash the embryogenic microspores may be especially in the form of Tris HCL (pH 8.0) as described in Sambrook, Fritsch & Maniatis (1989).

A preferred method of introducing the nucleic acid segments into embryogenic microspoes is to infect microspores with *A. tumefaciens* carrying an inserted DNA construct (see especially U.S. Pat. No. 5.188.958 and EP 0 270 615 B1).

The nucleic acid segments or constructs can be introduced into appropriate plant cells, for example, by means of the Ti plasmid of *A. tumefaciens*. The T-DNA is transmitted to embryogenic microspores upon infection by *A. tumefaciens*, and is stably integrated into the plant genome. Under appropriate conditions known in the art, the transformed embryogenic microspores develop further into plants.

The Agrobacterium strains customarily employed in the art of transformation are described, for example, in White (1993).

Ti plasmids contain two regions essential for the production of transformed cells. One of these, named transfer DNA (T DNA), induces tumor formation. The other, termed virulent region, is essential for the introduction of the T DNA into plants. The transfer DNA region, which transfers to the plant genome, can be increased in size by the insertion of the foreign nucleic acid sequence without its transferring ability being affected. By removing the tumor causing genes so that they no longer interfere the modified Ti plasmid ("disarmed Ti vector") can then be used as a vector for the transfer of the gene constructs of the invention into embryogenic microspores. In the binary system, to have infection, two plasmids are needed: a T-DNA containing plasmid and a vir plasmid. Any one of a number of T-DNA containing plasmids can be used, the only requirement is that one be able to select independently for each of the two plasmids (see especially EP 116718 B1 and EP 120 516 B1).

The embryogenic microspores with the integrated desired DNA sequence can be selected by an appropriate phenotypic marker. These phenotypic markers include, but are not limited to, antibiotic resistance, herbicide resistance or visual observation. Other phenotypic markers are known in the art and may be used in this invention.

The DNA constructs used in instant invention consist of a transcription initiation region and, under the control of the transcription initiation region, a DNA sequence to be transcribed. The DNA sequence may comprise a natural open reading frame including transcribed 5' and 3' flanking sequences. Alternatively, it may comprise an anti-sense sequence that encodes the complement of an RNA molecule or portion thereof (as desribed in EP 140 308 B1 and EP 223 399 B1).

The initiation regions may be used in a variety of contexts and in combination with a variety of sequences. The RNA coded sequences of a gene may be those of a natural gene, including the open reading frame for protein coding and frequently the 5' and 3' untranslated sequences. The RNA translational initiation sequences are included in the constructs, either from the promoter domain or from the attached coding sequences.

Attached to the above sequences are appropriate transcription termination and polyadenylation sequences.

Examples of the above sequences or genes to be expressed from the constructs of the subject invention include:

antisense or sense genes (for gene suppression);
genes for nutritionally important proteins: growth promoting factors, yield enhancing factors, e.g. an asparagine synthetase gene or an invertase gene;
genes for proteins giving protection to the plant under certain environmental conditions, e.g. proteins giving resistance to metal or other toxicity;
genes for stress related proteins giving tolerance to extremes of temperature, freezing, etc.
genes for proteins of specific commercial value;
genes causing increased level of proteins, e. g., enzymes of metabolic pathways,
genes causing increased levels of products of structural value to a plant host, e.g., herbicide resistance, fungus resistance, e.g. chitinase genes, glucanase genes, proteins synthesis inhibitor genes, ribosome inhibitory protein genes, viral resistance, e.g. ribozymes, virus coat protein genes.

The subject constructs will be prepared employing cloning vectors, where the sequences may be naturally occuring, mutated sequences, synthetic sequences, or combinations thereof. The cloning vectors are well known and comprise prokaryotic replication systems, markers for selection of transformed host cells, and restriction sites for insertion or substitution of sequences. For transcription and optimal expression, the DNA may be transformed into embryogenic microspores for integration into the genome, where the subject construct is joined to a marker for selection or is co-transformed with DNA encoding a marker for selection.

The selection of transformed embryogenic microspores is enabled by the use of a selectable marker gene which is also transferred. The expression of the marker gene confers a phenotypic trait that enables the selection. Examples for such genes are those coding for antibiotics or herbicide resistance, e.g. genes causing resistance against glutamine synthetase inhibitors, e.g. bialaphos or phosphinothricin resistance conferred by genes isolated from *Streptomyces hygroscopicus* or *iridochromogenes* (BAR/PAT). Other examples are the neomycin phosphotransferase or the glucuronidase gene.

The process claimed in instant invention provides a comparable number of effectively transformed embryogenic microspores. The efficiency of transformation was about two up to 15 percent. As efficiency we define here the number of transformed embryos (plants) related to the number of all embryos (plants) plated on the selection medium.

The transformation method using Agrobacterium is relatively simple, highly reproducible and has a high possibility of being extrapolated to other embryogenic microspore culture systems. In all species where microspores can developed into embryos (androgenesis), this method can be expected to generate transgenic haploid or doubled haploid plants in a one step procedure.

The class of transgenic embryogenic microspores which are covered by this invention is generally as broad as the class of higher plants amenable to androgenesis (development from microspores to embryos that develop into plants) and techniques developed to stimulate androgenesis including both monocotyledonous and dicotyledonous plants. It is known that theoretically all plants can be regenerated from cultured embryogenic microspores, including but not limited to all major cereal crop species, sugarcane, sugar beet, cotton, fruit and other trees, legumes and vegetables.

Accordingly, the use of embryogenic microspores will help to produce transformed plants in genotypes of cereal and legume species which are now considered recalcitrant. Although it has been shown that for example wheat, rice, maize can be transformed with Agrobacterium, broad success has been impeded greatly by the difficulty to direct the gene transfer towards plant cells that are amenable to regeneration (van Rordragen & Dons 1992). With increased knowledge about the biology of the infection process of Agrobacterium (Smith & Hood 1995) and the rapid development in cereal microspore culture, the use of embryogenic microspores will be especially suitable for the transformation of monocotyledons (Jähne and Lörz 1995). In the meantime it has been shown that even yeast can be transformed with *A. tumefaciens* (Piers et al. 1996).

Examples of families that are of special interest are Poaceae, but also Solanaceae and Brassicaceae.

Some suitable species include, for example, species from the genera Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Hyoscyamus, Lycopersicon, Nicotiana, Solanum, Petunia, Digitalis, Majorana, Ciohorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis. Browaalia, Glycine, Lolium, Zea, Triticum, Sorghum, and Datura.

Examples of species of commercial interest that can be protected include:
tobacco, *Nicotiana tabacum* L.
tomato, *Lycopersicon esculentum* Mill,
potato, *Solanum tuberosum* L.,
Canola/Rapeseed,
*Brassica napus* L.,
cabbage, broccoli, kale etc.,
*Brassica oleracea* L.,
mustards *Brassica juncea* L.,
*Brassica nigra* L.,
*Sinapis alba* L. (Brassicaceae),
petunia, *Petunia hybrida* (Solanaceae)
sugar beet, *Beta vulgaris*, (Chenopodiaceae),
cucumber, Curcurbita sp. (Curcurbitaceae),
cotton, Gossypium sp., (Malvaceae),
sunflower, *Helianthus annuus*,
lettuce *Lactuca sativa*, (Asteraceae=Compositae),
pea, *Pisum sativum*,
soybean, *Glycine max* and alfalfa, Medicago sp. (Fabaceae=Leguminoseae),
asparagus, *Asparagus officinalis;*
gladiolus, Gladiolus sp., (Lilaceae);
corn, *Zea mays;*
rice, *Oryza sativa* (Poaceae);
wheat, *Triticum aestivum* (Poaceae); and
barley, *Hordeum vulgare* (Poaceae).

In an preferred embodiment the invention covers transformed embryogenic microspores in the Brassica species for example *B. napus, B. rapa, B. juncea, B. oleracea, B. carinata* and others.

The invention additionally relates to Brassica plants which have been regenerated out of embryogenic microspores which have been transformed according to instant invention.

The present invention is directed to the use of embryogenic microspores for a new haploid transformation system. Microspores refers to freshly isolated microspores up to 72 hours after isolation which comprise mainly of single cells as the first cell division is usually visible three days after culture. The microspore system offers advantages over other explant methods in that regeneration leads to the production of haploid plants or homozygous diploid plants. This offers simplicity for genetic studies and one-step fixation of genes for breeding purposes.

The use of embryogenic microspores for transformation can be carried out as described in the materials and methods and in the examples.

In general, preparation of plasmid DNA, restriction enzyme digestion, agarose gel electrophoresis of DNA, Southern blots, DNA ligation and bacterial transformation were carried out using standard methods. (Sambrook I. et al. (1989), referred to herein as "Maniatis" and hereby incorporated by reference.)

3. MATERIALS AND METHODS

The following disclosure describes the use of embryogenic microspores and the tranformation process. The disclosure will then be completed with the description of the conditions under which embryogenic microspores can be transformed, also merely by way of examples for non-limitative illustration purposes.

*A. tumefaciens* cells (MP90RK with pHoe6Ac, see FIG. 1) (diluted $10^{-4}$ to $10^{-7}$ times from a 0.9 O.D. spectrophotometric standard) were added to freshly isolated microspores or microspores cultured up to 72 h. A dilution of $10^{-5}$ corresponds to a concentration of approximately 10,000 Agrobacteria per ml. The cultures were supplemented with cellolytic enzymes and incubated for 72 hours following the temperature regime described by Baillie et al. (1992).

For one experiment usually 5 petridishes have been filled with microspores harvested from about three plants. One petri dish contains approximately the microspores from 10 flower buds.

Subsequently (after three days of cocultivation), the cultures were washed gently by discarding the supernatant and adding fresh NLN medium containing 10% sucrose sucrose with 500 mg/l carbenicillin (or 300 mg/l Timentin). As the microspores adhere tightly to the bottom of the petri plate at this stage of infection, there is very little loss of microspores.

The microspores adhering to the bottom of the petri plates are then gently scraped and loosened from the bottom of the plate using soft rubber policemen (Fisher Scientific). Then the fresh medium and microspores were transferred into 50 ml Falcon tubes for centrifugation.

Centrifugation was carried out two times for three minutes (at 200 g). Microspores were suspended and centrifuged at least once in lysozyme and 10 mM Tris HCL. buffer pH 8.0. Finally fresh NLN medium plus 10% sucrose and 500 mg/l carbenicillin (or 300 mg/l Timentin) was added and the cultures were incubated according to Baillie et al. 1992.

The cultures are kept at 24° C. until they are four weeks old as the developing embryos are usually a week slower than non-infected control embryos.

Selection for true transformants can be started as soon as embryos become visible, the selection is preferably carried out after greening of the embryos has started.

The timeframe from microspore isolation until transformed plantlet in the greenhouse takes approximately three months.

The following examples are intended only to further illustrate the invention and are not intended to limit the scope of the invention which is defined by the claims.

4. EXPERIMENTAL DATA 4.1. Optimization of Co-cultivation Conditions for Improved Embryo Recovery and Transformation Efficiency Material: Fresh buds of Brassica rapa, CV2

DNA construct: glufosinate (Phosphinothricin, L-PPT) resistance gene under control of 35S promotor and 35S terminator (Plasmid pRD 320 having the same sequence as pRD 420 (Datla et al. 1992) but with the PAT gene).

Preculture: Incubator (10/5° C., 16 h photoperiod)

| Treatment | A (Control) | B | C | D | E |
|---|---|---|---|---|---|
| day 0 | Initiaton of microspore culture | Infection with cellulase | Infection without cellulase | Infection with cellulase | Infection without cellulase |
| day 2 | Transfer | Transfer | Transfer | Transfer | Transfer |
| day 3 | centrifuge wash | centrifuge wash | hand wash | centrifuge wash | hand wash |
| day 23 | 490 embryos/plate | 12 embryos/plate | 16 embryos/plate | 18 embryos/plate | 24 embryos/plate |
| day 30 | greening | greening | greening | greening | greening |
| day 39 | plating | plating | plating | plating | plating |
| day 54 | rooting assay | rooting assay | rooting assay | rooting assay | rooting assay |
| day 59 | 0 | 10 | 4 | 11 | 6 |

A: Control (uninfected)
B: + cellulase + Agrobacterium ($10^{-6}$)
C: + cellulase + Agrobacterium ($10^{-6}$)
D: + cellulase + Agrobacterium ($10^{-7}$)
E: − cellulase + Agrobacterium ($10^{-7}$)
day 0: Initiation of microspore culture after Baillie (1992) but without amino acids. Infection with A. tumefaciens and addition of cellulase where applicable. Incubation for two days at 32° C.
day 2: Transfer of plates to 24° C. incubator.
day 3: Media change to NLN10. Centrifuge wash was performed 2 times at 200 g.
day 23: Embryo count.
day 30: Greening up of embryos under continous light at 22° C. on shaker at 75 rpm.
day 39: Plating on OB5 solid medium.
day 54: Start L-PPT rooting assay (Selection on 20 mg/l L-PPT).
day 59: Transfer of putative transformants to OB5 solid medium.

The data for the recovered embryos and putative transformants are summarized in the attached graphics. The results show that the addition of cellulase does not only dissolve the fibrils of the Agrobacteria to enable centrifuge wash, but also increased transformation efficiency, obviously by dissolving cellulose of the plant material. Cellulase on the other hand reduced the number of embryos recovered slightly within each level of the tested Agrobacterium concentration.

4.2. Comparison of the Effect of Different Washing Procedures on Embryo Yield After Infection with A. tumefaciens Material: Buds of Brassica rapa, CV2
DNA construct: pHoe6Ac (see FIG. 1, AC stand for Acetyltransferase, i.e. PAT)
Preculture: Incubator (10/5° C., 16 h photoperiod), flower buds stored at 4° C. for two days prior to micorspore culture.

| | A (Control) | B | C | D | E |
|---|---|---|---|---|---|
| day 0 | Initiation + | Initiation | Initiation | Initiation | Initiation |
| day 3 | transfer | Infection and transfer | Infection and transfer | Infection and transfer | Infection and transfer |
| day 5 | — | — | — | + cellulase | + cellulase |
| day 6 | Centrifuge wash media change | Centrifuge wash media change | Hand wash media change (lots of | Centrifuge wash media change (fibrils | Centrifuge wash + lysozyme media change |
| day 22 | 484 embryos/plate | lysozyme treatment 390 embryos/plate | connected fibrils) no embryos | dissolved) 27 embryos/plate | (fibrils dissolved) 58 embryos/plate |

A: uninfected control,
B: uninfected control and the application of lysozyme during media change,
C: hand wash at day 6,
D: Addition of cellulase at day 5 and centrifuge wash at day 6,
E: as D but with additional lysozyme treatment at day 6.
day 0: Initiation of microspore culture after Baillie (1992) but without amino acids. Incubation for two days at 32° C.
day 3: Infection with Agrobacterium and transfer of plates to 24° C. incubator.
day 5: Addition of cellulase.
day 6: Wash: Centrifuge wash where applicable at 200 g. Lysozyme treatment where applicable. Media change to NLN10 in all treatments.
day 22: Embryo count: Lysozyme treatment doubled the number of recovered embryos. Mean number of embryos of E differs significantly from C (tested with 8 replicates per treatment).

4.3. Generation of Transformants Carrying Disease Reistance Genes

Figure 2:
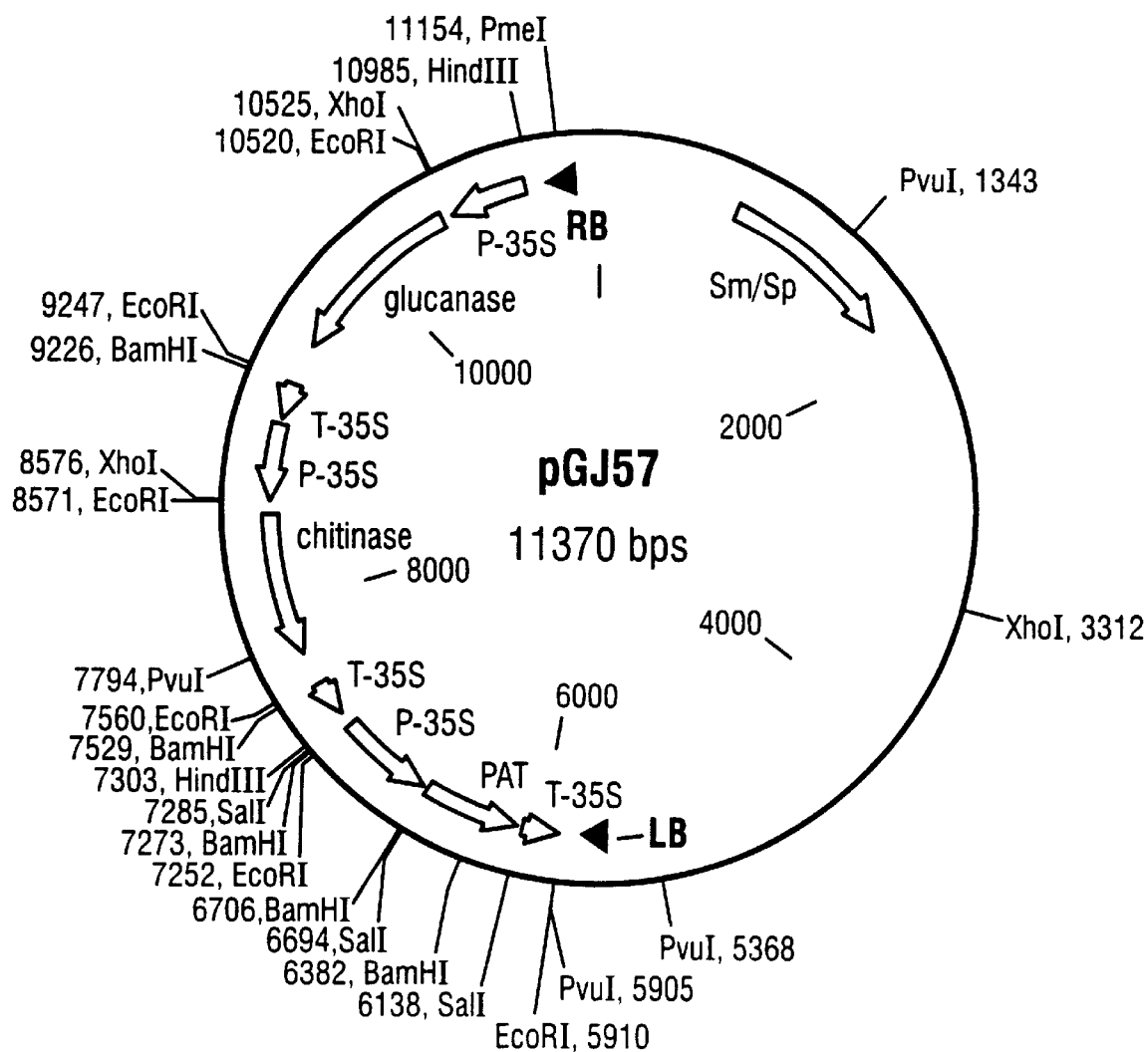

Material: Brassica napus, Topaz 4079
DNA construct: pGJ57 (Glucanase, Chitinase, PAT each with 35S terminator and 35 S promoter, see FIG. 2)
Preculture: Incubator (10/5° C., 16 h photoperiod), flower buds, stored at 4° C. for two days prior to initiation of microspore culture.

| | A (Control) | B |
|---|---|---|
| day 0 | Initiation of microspore culture[x1] | Initiation of microspore culture |
| day 1 | — | Infection with Agrobacterium |
| day 3 | Transfer | Transfer |
| day 4 | Centrifuge wash | Centrifuge wash + lysozyme treatment |
| day 22 | 422 embryos/plate | 70 embryos/plate |
| day 60 | 50 healthy plants | 50 healthy plants |
| day 66 | 0 | $2^{x2}$ |

[x1]Each treatment comprises five plates. Per plate approximately ten flower buds have to be harvested
[x2]Fifty healthy plants were transferred to selection medium. Out of fifty two independent transformants were selected. This represents a transformation frequency of 4%. The two transformants were confirmed via Southern analysis.
A: uninfected control,
B: As A but infected with A. tumefaciens ($10^{-6}$)
day 0: Initiation of microspore culture. Incubation for two days at 32° C.
day 1: Infection with A. tumefaciens where applicable and addition of colchicine
day 3: Transfer of plates to 24° C. incubator
day 4: Centrifuge wash was performed 2 times at 200 g. Lysozyme treatment. Media change to NLN10.
day 22: Embryo count.
day 60: Start L-PPT Rooting Assay (20 mg/l L-PPT).
day 66: Transfer of putative transformants to OB5 solid medium.

It is understood that the foregoing detailed description is given merely by way of illustration and that modification and variations may be made therin without departing from the spirit and scope of the invention.

5. REFERENCES

Arnoldo, M. (1992) Development of an efficient Agrobacterium-mediated transformation system in Brassica napus. Canada: University of Toronto; Thesis Baillie, A. M. R., Epp, D. J., Hutcheson, D., Keller, W. A. (1992) In vitro culture of isolated microspores and regeneration of plants in *Brassica campestris* Plant Cell Rep 11: 234–237.

Christou Paul (1995) Strategies for variety-independent genetic transformation of important cereals, legumes and woody species utilizing particle bombardment. Euphytica, 85, 13–27.

Creissen, G., Smith, C., Francis, R., Reynolds, H., Mullineaux, P. (1990) Agrobacterium- and microprojectile-mediated viral DNA delivery into barley microspore-derived cultures. Plant Cell Rep., 8, 680–683.

Datla R. S. S., J. Hammerlindl, B. Panchuk, L. Pelcher, W. Keller (1992) Modified binary plant transformation vectors with the wild type gene encoding NPTII, Gene, 2 (11), 383–384.

Fennell, A., Hauptmann, R. (1992) Electroporation and PEG delivery of DNA into maize microspores. Plant Cell Rep., 11, 567–570.

Heberle-Bors E. (1989) EPO 301 316 (Chemie Holding AG).

Heberle-Bors Erwin (1995) Transformation via microspore embryogenesis, Rice Biotechnology Quarterly, Vol. 23, 17–18.

Huang, B. (1992) Genetic manipulation of microspores and microspore-derived embryos. In Vitro Cell. Dev. Biol. 28P, 53–58. (Review)

Jardinaud, M-F., Souvré, A., Alibert, G. (1993) Transient GUS gene expression in *Brassica napus* electroporated microspores. Plant Sci 93, 177–184.

Jardinaud M. F., A. Souvré, G. Alibert, M. Beckert (1995) uidA gene transfer and expression in maize microspores using the biolistic method, Protoplasma, 187 (1–4), 138–143.

Jähne A. and H. Lörz (1995) Cereal microspore culture, Plant Science, 109, 1–12.

Jähne A., D. Becker, R. Brettschneider & H. Lörz (1994) Regeneration of transgenic, microspore-derived, fertile barley, Theor. Appl. Genet., 89, 525–533.

Jones-Willenuve, Bin Huang, I. Prudhomme, S. Bird, R. Kemble, J. Hattori & B. Miki (1995) Assessment of microinjection for introducing DNA into uninuclear microspores of rapeseed, Plant Cell Tissue and Organ Culture, 40, 97–100.

Moeller C., M. Iqbal and G. Roebellen (1994) Efficient production of doubled haploid *Brassica napus* plants by colchicine treatment of microspores, Euphytica 75 (1–2) 95–104.

Neuhaus, G., Spangenberg, G., Mittelsten Scheid, O., Schweiger, H-G. (1987) Transgenic rapeseed plants obtained by the microinjection of DNA into microspore-derived embryoids. Theor Appl. Genet 75, 30–36.

Pechan, P. M. (1989) Successful cocultivation of *Brassica napus* microspores and proembryos with Agrobacterium. Plant Cell Rep 8: 387–390.

Potrykus I. (1991) Gene transfer to plants: Assessment of published approaches and results, Ann. Rev. Plant Physiol. Plant Mol. Biol., 42, 205–225.

Potrykus I. (1993) Gene transfer to plants: approaches and available techniques, In: Hayward et al. (Eds.) Plant Breeding—Principles and prospects, Chapman & Hall, 126–137.

Piers K. L., J. D. Heath, X. Liang, K. M. Stephens and E. W. Nester (1996) *Agrobacterium tumefaciens*-mediated transformation of yeast, Microbiology, 93, 1613–1618.

Sambrook I., E. F. Fritsch, T. Maniatis (1989) Molecular cloining: a laboratory manual. Cold Spring Harobr Laboratory Press.

Sangawan R. S., C. Ducrocq, B. Sangwan-Noorreel (1993) Agrobacterium-mediated transformation of pollen embryos in *Datura innoxia* and *Nicotiana tabacum*: production of transgenic haploid and fertile homozygous diploid plants, Plant Science, 95, 99–115.

Smith R & E. Hood (1995) *Agrobacterium tumefaciens* transformation of monocotyledons, Crop Science, 35 (2), 301–309.

Swanson, E. B., Erickson, L. R. (1989) Haploid transformation in *Brassica napus* using an octopine-producing strain of *Agrobacterium tumefaciens*. Theor. Appl. Genet. 78, 831–835.

Stöger E., C. Fink, M. Pfosser & E. Herberle-Bors (1995) Plant transformation by particle bombardment of embryogenic pollen, Plant Cell Reports, 14, 273–278.

Thierfelder A., W. Lühs & W. Friedt (1993) Breeding of industrial oil crops with the aid of biotechnoloogy: a review, Industrial Crops and Products, 1, 261–271.

White F. F. (1993) Vectors for gene transfer in higher plants, In: Kung S. and R. Wu (Eds.) Transgenic Plants, Vol. 1, 15–48.

Wordragen van M. F. & H. J. M. Dons (1992) Agrobacterium tumeffaciens-mediated transformation of recalcitrant crops, Plant Molecular Biology Reporter, 10(1), 12–36.

Zhao J., D. H. Simmonds (1995) Application of trifluralin to embryryogenic microspore cultures to generate doubled haploid plants in *Brassica napus*, Physiologia Plantarum, 95 (2), 304–309.

6. FIG. 2—LEGEND

| | | | Molecular Features | | |
| --- | --- | --- | --- | --- | --- |
| Type | Start | End | Compl | Name | Description |
| GENE | 790 | 1758 | | Sm/Sp | strep/spec adenyltransferase |
| GENE | 5611 | 5634 | | LB | left border from octopine Ti ACH5 |
| GENE | 6123 | 5917 | (C) | T-35S | CaMV 35S terminator |
| GENE | 6693 | 6142 | (C) | PAT | synthetic PAT gene |
| GENE | 7251 | 6722 | (C) | P-35S | CaMV 35S promoter |
| GENE | 7519 | 7324 | (C) | T-35S | 35S terminator |
| GENE | 8506 | 7706 | (C) | chitinase | chitinase |
| GENE | 9000 | 8582 | (C) | P-35S | 35S promoter |
| GENE | 9216 | 9021 | (C) | T-35S | 35S terminator |
| GENE | 10483 | 9467 | (C) | glucanase | glucanase |
| GENE | 10949 | 10531 | (C) | p-35S | 35S promoter |
| GENE | 11173 | 11196 | | RB | right border from pTiT37 |

What is claimed is:

1. A method for producing a stably transformed Brassica embryogenic microspore, capable of leading to a non-chimeric transformed haploid or doubled haploid embryo which develops into a fertile homozygous Brassica plant within one generation, said process comprising the following steps:

a. infecting an embryogenic microspore with Agrobacteria, which contain a plasmid carrying a gene of interest under regulatory control of initiation and termination signals bordered by at least one T-DNA border, and b. washing out and killing the Agrobacteria after co-cultivation using mucolytic enzymes, thereby producing a stably transformed Brassica embryogenic microspore.

2. A method for producing a non-chimeric Brassica plant, containing a foreign DNA stably incorporated into its genome, said method comprising:

a. co-cultivating a Brassica embryogenic microspore with Agrobacteria which contains a plasmid carrying a gene of interest under regulatory control of initiation and termination signals;

b. washing out and killing the Agrobacteria after co-cultivation using mucolytic enzymes; and c. regenerating a non-chimeric haploid or doubled haploid Brassica embryo from said microspore, wherein the embryo contains said gene of interest stably integrated into its genome, thereby producing a non-chimeric Brassica plant.

3. The method according to claim 1, further comprising the step of adding cellolytic enzymes during Agrobacterium co-cultivation.

4. The method according to claim 3, wherein said cellolytic enzyme is a cellulase.

5. The method according to claim 1, wherein the mucolytic enzyme is a lysozyme.

6. The method according to claim 2, further comprising the step of adding cellolytic enzymes during Agrobacterium co-cultivation.

7. The method according to claim 6, wherein said cellolytic enzyme is a cellulase.

8. The method according to claim 2, wherein the mucolytic enzyme is a lysozyme.

\* \* \* \* \*